US009555405B2

(12) United States Patent
Wang et al.

(10) Patent No.: US 9,555,405 B2
(45) Date of Patent: Jan. 31, 2017

(54) NANOPARTICLE CATALYST CAPABLE OF FORMING AROMATIC HYDROCARBONS FROM $CO_2$ AND $H_2$

(71) Applicant: Kansas State University Research Foundation, Manhattan, KS (US)

(72) Inventors: Hongwang Wang, Manhattan, KS (US); Stefan H. Bossmann, Manhattan, KS (US); Donghai Wang, Manhattan, KS (US); Deryl L. Troyer, Manhattan, KS (US); Tej Shrestha, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 7 days.

(21) Appl. No.: 14/603,628

(22) Filed: Jan. 23, 2015

(65) Prior Publication Data
US 2015/0141238 A1 May 21, 2015

Related U.S. Application Data

(63) Continuation-in-part of application No. PCT/US2013/051854, filed on Jul. 24, 2013.
(Continued)

(51) Int. Cl.
*C07C 1/04* (2006.01)
*C07C 15/00* (2006.01)
(Continued)

(52) U.S. Cl.
CPC ............... *B01J 35/026* (2013.01); *B01J 21/04* (2013.01); *B01J 23/745* (2013.01); *B01J 29/106* (2013.01);
(Continued)

(58) Field of Classification Search
CPC ..... B01J 23/745; B01J 35/0006; B01J 35/023; B01J 35/08; C07C 1/12; C07C 1/04; C07C 1/10; C07C 15/04; C07C 15/06; C07C 15/08
See application file for complete search history.

(56) References Cited

U.S. PATENT DOCUMENTS

| 4,565,831 A | 1/1986 | Wright et al. |
| 5,215,648 A | 6/1993 | Zones et al. |
| 8,877,951 B2 * | 11/2014 | Wang ............ B01J 31/08 549/498 |

FOREIGN PATENT DOCUMENTS

EP        039964        11/1981

OTHER PUBLICATIONS

Bychko, I.B.; Kalishin, E.Y.; Strizhak, P.E. Theoretical and Experimental Chemistry, 2011, 47, 219-224.*
(Continued)

*Primary Examiner* — Rip A Lee
(74) *Attorney, Agent, or Firm* — Hovey Williams LLP

(57) ABSTRACT

Nanocatalysts and methods of using the same to obtain aromatic hydrocarbon compounds from a source of carbon atoms and a source of hydrogen atoms in a single reaction step is provided. The catalyst comprises an $Fe/Fe_3O_4$ nanocatalyst that may be supported on a non-reactive support material such as a zeolite or alumina. $CO_2$ and $H_2$ are preferred sources of carbon and hydrogen atoms for the reaction. The aromatic hydrocarbon compounds produced are suitable for direct usage as fuel without need for further refining.

30 Claims, 3 Drawing Sheets

(a)        (b)

Related U.S. Application Data

(60) Provisional application No. 61/675,118, filed on Jul. 24, 2012.

(51) Int. Cl.

| | | |
|---|---|---|
| *B01J 23/74* | (2006.01) | |
| *B01J 23/94* | (2006.01) | |
| *B01J 35/02* | (2006.01) | |
| *B01J 23/745* | (2006.01) | |
| *C07C 1/12* | (2006.01) | |
| *B01J 29/14* | (2006.01) | |
| *B01J 35/00* | (2006.01) | |
| *B01J 21/04* | (2006.01) | |
| *B01J 29/10* | (2006.01) | |
| *C07C 1/22* | (2006.01) | |
| *C10L 1/04* | (2006.01) | |
| *B82Y 40/00* | (2011.01) | |

(52) U.S. Cl.
CPC .............. *B01J 29/146* (2013.01); *B01J 35/002* (2013.01); *B01J 35/006* (2013.01); *B01J 35/008* (2013.01); *B01J 35/0013* (2013.01); *B01J 35/0033* (2013.01); *B01J 35/0053* (2013.01); *C07C 1/12* (2013.01); *C07C 1/22* (2013.01); *C10L 1/04* (2013.01); *B01J 2229/186* (2013.01); *B82Y 40/00* (2013.01); *C07C 1/044* (2013.01); *C07C 2523/745* (2013.01); *C10L 2200/0469* (2013.01); *C10L 2200/0492* (2013.01); *Y02P 20/52* (2015.11)

(56) References Cited

OTHER PUBLICATIONS

Wang, H.; Wu, X.; Wang, D.; Hodgson, J.; Bossmann, S.H. Prepr. Pap.-Am. Chem. Soc., Div. Energy Fuels Chem. 2012, 57, 396.*
Bychko et al. Advances in Materials Physics and Chemistry, 2012, 2, 17-22.*
Peng S.; Sun, S. Angew. Chem. Int. Ed. 2007, 46, 4155-4158.*
Bahome et al. Applied Catalysis A: General 2005, 287, 60-67.*
Balivada et al. BMC Cancer 2010, 10:119.*
Jahangirian et al. Digest Jounal of Nanomaterials and Biostructures 2013, 8, 1405-1413.*
Mendoza-Bello et al. J. Nanopart. Res. 2012, 14:1242.*
Wang et al. Prepr. Pap.-Am. Chem. Soc., Div. Energy Fuels Chem. 2012, 57(2), 177-178.*
Bychko, Igor, "TPR Study of Core-Shell FE@FE2O4 Nanoparticles Supported on Activated Carbon and Carbon Nanotubes" Advances in Materials Physics and Chemistry, Scientific Research, 2, 1—pp. 17-22, Mar. 2012.
Pour, Ali Nakhaei, "Fischer-Tropsch Sunthesis by Nano-Structured Iron Catalyst" Jornal of Natural Gas Chemistry, vol. 19 No. 3, pp. 284-292, 2010.
Ong, Guy Khac "Role of Frozen Spins in the Exchange Anisotropy of Core-Shell Fe@Fe3O4 Nanoparticles" Journal of Physical Chemistry, v. 115, pp. 2665-2672, 2011.
Sarkar, Amitava "Fischer-Tropsch Synthesis: Morphology, Phase Transformation and Particle Size Growth of Nano-scale Paricles" Catal Lett, v. 117, pp. 1-17; Springer Science + Business Media, LLC; Jul. 20, 2007.
Tie, Shao-Long "Monodisperse Fe3O4/Fe@SiO2 core/shell Nanoparticles with Enhanced Magnetic Property" Colloids and Surfaces A: Physicochem. Eng. Aspects vol. 293, pp. 278-285, Aug. 2, 2006.
The International Search Report and Written Opinion dated Nov. 27, 2013, in the corresponding PCT/US13/51854 filed Jul. 24, 2013.
Smit, Emiel "On the Surface Chemistry of Iron Oxides in Reactive Gas Atmospheres" Angew. Chem. Int. vol. 50, 1584-1588, Ed. 2011.
Mogorosi, Ramoshibidu P. "Strong-Metal-Support Interaction by Molecular Design: Fe-silicate Interactions in Fischer-Tropsch Catalysts" Journal of Catalysis, vol. 289 pp. 140-150, 2012.
Torres Galvis, Hirsa M. "Supported Iron Nanoparticles as Catalysts for Sustainable Production of Lower Olefins" Science magazine vol. 335 Feb. 17, 2012. downloaded on Jul. 18, 2012.

* cited by examiner

NANOPARTICLE CATALYST CAPABLE OF FORMING AROMATIC HYDROCARBONS FROM $CO_2$ AND $H_2$

RELATED APPLICATION

The present application is a continuation-in-part of International Patent Application No. PCT/US2013/051854 filed Jul. 24, 2013, which claims the benefit of U.S. Provisional Patent Application No. 61/675,118, filed Jul. 24, 2012, incorporated by reference herein in its entirety.

STATEMENT REGARDING FEDERALLY SPONSORED RESEARCH

This invention was made with U.S. Government support under grant number EPS-0903806 awarded by the National Science Foundation. The government has certain rights in the invention.

BACKGROUND OF THE INVENTION

Field of the Invention

The present invention is generally directed toward nanocatalysts and methods of using such catalysts to synthesize aromatic hydrocarbon compounds from carbon dioxide and hydrogen mixtures under relatively mild reaction conditions. Particularly, the catalyst comprises an $Fe/Fe_3O_4$ nanocatalyst that may be supported on a non-reactive support material such as a zeolite or alumina. The aromatic hydrocarbon compounds produced are suitable for direct usage as fuel without need for further refining.

Description of the Prior Art

The diminishing fossil fuel reserves and ever-increasing $CO_2$ emissions have created great concern amongst the scientific community. Since the industrial revolution, a significant increase of $CO_2$ concentration in the atmosphere has been witnessed due to the combustion of carbon-rich fossil fuels, consequently, leading to global warming and drastic climate changes. As a result, the quest for renewable and cleaner energy sources to meet the fast population and economic growth is more urgent than ever before. Being the most abundant carbon source in earth's atmosphere, $CO_2$ can be used as a cheap and non-toxic C1 building block in many chemical processes. Hydrogenation of $CO_2$ to produce methanol and dimethylether (DME), as well as hydrocarbons is attractive, not only because these products are excellent fuels for internal combustion engines, but also because the whole process is considered to be cleaner, sustainable, and carbon-neutral (for example, using $CO_2$ from atmosphere, $H_2$ from water splitting and sunlight for energy). However, their chemical and physical properties, are inferior to conventional gasoline. Our distribution systems were developed for liquid fuel. It is easier and less costly to use the existing distribution infrastructure instead of building a new distribution system for methane or hydrogen. Liquid fuels are also safer than gaseous fuels: 1000 atmospheres (14,696 psi) of $CH_4$ or $H_2$ have the same density than 1 L of liquid fuels at room temperature. However, liquid fuels are much less in danger of explosion during accidents.

Although methane has a high octane number (120), it is not useful for classic combustion engines. Mesitylene, octane number: 110, xylenes: 115-120, toluene: 111 make excellent components of high-octane fuel (86 to 92 in the US). Finally, whereas the long-term storage of hydrogen is very difficult, a mixture of aromatic hydrocarbons can be easily stored for fuel or synthesis application.

Iron-based heterogeneous catalysts have been intensively studied for the $CO_2$ hydrogenation reaction. Earlier research showed that bulk iron or iron oxides catalyze $CO_2$ hydrogenation, which mainly produce methane as product. These catalysts were rapidly deactivated due to carbon deposition. Doping of promoters such as potassium, manganese, and copper had significant effect on both the reactivity and selectivity of the iron-based catalysts. Higher olefins and aliphatic hydrocarbons, as well as improved $CO_2$ conversion, were achieved. $Al_2O_3$ was found to be an excellent structure promoter to sustain the catalyst activity of iron-based catalysts by preventing sintering of active particles during the reaction. When using zeolites as solid supports, the product's distribution was highly dependent on the structure and acidity of the zeolites. The iron-zeolite composites were also reported as dual functional catalysts that promoted multi-step transformation for $CO_2$ hydrogenation.

In spite of all the efforts during the last decades, the direct formation of aromatic hydrocarbons in a one-step reaction from carbon dioxide, without forming aliphatic hydrocarbons first, remains elusive.

SUMMARY OF THE INVENTION

According to embodiments of the present invention, aromatic hydrocarbon compounds are obtained from carbon dioxide and hydrogen mixtures using an $Fe/Fe_3O_4$ nanocatalyst at relatively low reaction vessel pressures and relatively mild reaction temperatures.

According to one embodiment of the present invention there is provided a method of synthesizing one or more aromatic hydrocarbon compounds. A quantity of a catalytic material comprising $Fe/Fe_3O_4$ core/shell nanoparticles is provided within a reactor. A quantity of reactants comprising a source of carbon atoms and a source of hydrogen atoms is introduced into the reactor and contacted with the catalytic material. The reactants are reacted within the reactor under conditions for forming the one or more aromatic hydrocarbon compounds. The one or more aromatic hydrocarbon compounds are then recovered from the reactor.

In one particular embodiment of the present invention, the method of synthesizing one or more aromatic hydrocarbon compounds comprises providing within a reactor a quantity of a catalytic material comprising $Fe/Fe_3O_4$ core/shell nanoparticles. A quantity of reactants comprising a source of carbon atoms and a source of hydrogen atoms are introduced into the reactor and contacted with the catalytic material. The source of carbon atoms is selected from the group consisting of lignin, $CO_2$, CO, and combinations thereof. The source of hydrogen atoms is selected from the group consisting of $H_2$, $H_2O$, $CH_4$, and combinations thereof. The reactants are reacted within the reactor under conditions for forming the one or more aromatic hydrocarbon compounds. The conditions within the reactor comprise a temperature of between about 380° C. to about 560° C., and a pressure of between about 1 to about 1.1 atm. The one or more aromatic hydrocarbon compounds are then removed from the reactor. The one or more aromatic hydrocarbon compounds recovered are selected from the group consisting of xylenes, toluene, benzene, and mixtures thereof. Moreover, the aromatic hydrocarbon compounds comprising at least 75% by weight of the total reaction products produced by the reacting step.

In another embodiment of the present invention there is provided a system for synthesizing one or more aromatic hydrocarbon compounds. The system comprises a reactor comprising a quantity of a catalytic material comprising Fe/Fe$_3$O$_4$ core/shell nanoparticles, one or more reactant feed streams coupled with the reactor and operable to deliver to the reactor a source of carbon atoms and a source of hydrogen atoms, and a reaction product discharge stream coupled with the reactor and operable to remove the one or more aromatic hydrocarbon compounds from the reactor. The reactor operates under conditions for reacting the source of carbon atoms and the source of hydrogen atoms in the presence of the catalytic material for forming the one or more aromatic hydrocarbon compounds.

According to yet another embodiment of the present invention there is provided a method of synthesizing Fe/Fe$_3$O$_4$ core/shell nanoparticles on a non-reactive support material. A reaction mixture is provided within a reaction vessel. The reaction mixture comprises a C10-C24 alkene solvent, a C10-C24 amine having at least one ethylenically unsaturated group, a C4-C24 ammonium salt, and a non-reactive support material. The reaction mixture is heated to a temperature of between about 150° C. to about 210° C. A quantity of Fe(CO)$_5$ is added to the reaction mixture and reacted with the C10-C24 amine and C4-C24 ammonium salt so as to form a plurality of Fe/Fe$_3$O$_4$ core/shell nanoparticles on the non-reactive support. The Fe/Fe$_3$O$_4$ nanoparticles comprise an outer organic ligand monolayer formed from at least portions of the C10-C24 amine and/or the C4-C24 ammonium salt. The Fe/Fe$_3$O$_4$ nanoparticles on said non-reactive support are then recovered from the reaction vessel.

DETAILED DESCRIPTION OF THE PREFERRED EMBODIMENT

Figure 1:
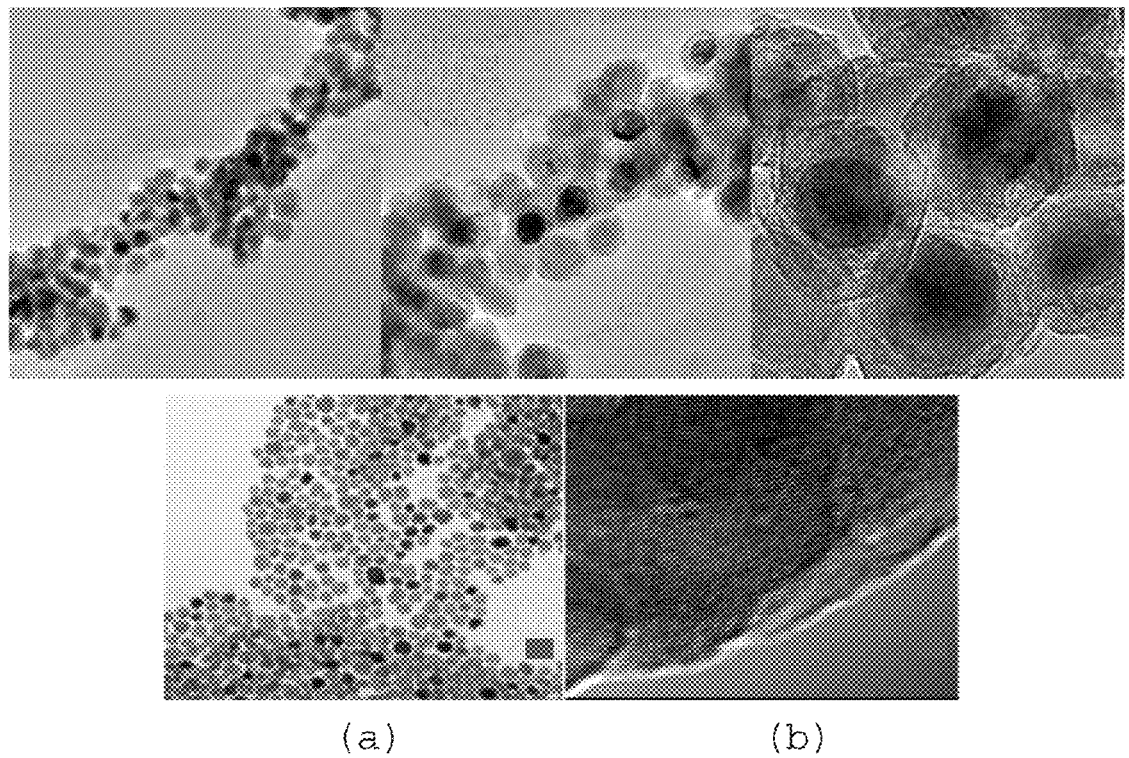
FIG. 1 is a TEM and HRTEM of Fe/Fe$_3$O$_4$ nanoparticles prepared by thermal decomposition of Fe(CO)$_5$ in the presence of oleylamine and HADxHCl.

The present invention is concerned with novel "Fischer-Tropsch" nanocatalysts for formation of hydrocarbon compounds, and specifically aromatic hydrocarbons as the major fraction of the reaction product. Catalysts used with the present invention are capable of forming aromatic hydrocarbons directly in a single step at relatively low temperatures (300-560° C.), and without further refining or processing of the reaction product. Existing catalysts start from aliphatic hydrocarbons or other waxy semisolids and convert them to aromatic hydrocarbons at temperatures exceeding 1000° C.

The Fischer-Tropsch reaction is generally described by the following reaction:

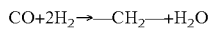

However, in one embodiment according to the present invention, the reaction is summarized by the following:

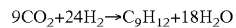

In certain embodiments, the nanocatalysts used with the present invention comprise core/shell nanoparticles of iron cores with iron oxide shells, and have an average (mean) diameter of less than about 20 nm, preferably from about 10 to about 20 nm. Preferably, the catalysts are Fe/Fe$_3$O$_4$ nanoparticles. The nanoparticles have a BET surface area of from about 20 to about 75 m$^2$/g, preferably about 23 to about 40 m$^2$/g. The nanoparticles have highly crystalline structures formed of nanolattices and comprise both crystalline cores and crystalline shells. Before activation, the catalysts can further comprise an organic ligand monolayer adjacent the shell; however, this ligand layer is removed after the first catalytic reaction to activate the catalyst, and is not a required component for the initial or subsequent reactions. The nanoparticles are not otherwise functionalized, and are preferably free of silane coatings or the like.

In certain embodiments, the nanocatalysts are supported on a non-reactive support material. For example, the non-reactive support can be a zeolite, aluminum silicate, or α-alumina, main group element oxide, d-block element oxide and f-block element oxide particles. In certain embodiments the α-alumina particles have a surface area of between about 100 to about 400 m$^2$/g, and preferably between about 250 to about 350 m$^2$/g (after calcination at 600° C.). Also, the surface area of the zeolite, such as zeolite Y, is preferably between about 500 and about 700 m$^2$/g.

Although not required, and in certain embodiments it is not present, a promoter material may be added to the nanocatalytic material in order to improve the catalyst performance and/or product selectivity. In certain embodiments the promoter comprises one or more metal ions such as potassium, manganese, zinc, or copper ions. In particular embodiments, the promoter is introduced into the nanocatalytic material as K$_2$CO$_3$, ZnCO$_3$, or a mixture thereof.

In methods of synthesizing the nanocatalyst, the Fe/Fe$_3$O$_4$ nanoparticles are actually grown upon the support material, as opposed to first being synthesized and then deposited or impregnated into the support. According to one embodiment of the present invention, the nanocatalyst is synthesized by first providing a reaction mixture within a reaction vessel. The reaction mixture comprises a C10-C24 alkene solvent, a C10-C24 amine having at least one ethylenically unsaturated group, a C4-C24 ammonium salt, and the non-reactive support material. In preferred embodiments, the C10-C24 alkene solvent is 1-octadecene, and the C10-C24 amine is oleylamine. Further, in certain embodiments, the C4-C24 ammonium salt is selected from the group consisting of C8-C22 primary alkyl ammonium salts, C4-C24 quaternary ammonium salts, and combinations thereof. In particularly preferred embodiments, the C8-C22 primary alkyl ammonium salt is hexadecylammonium chloride ad the C4-C24 quaternary alkyl ammonium salt is tetraethylammonium chloride.

The reaction mixture may then be heated to a temperature of between about 150° C. to about 210° C., or 160° C. to about 200° C., or about 180° C., at which point a quantity of Fe(CO)$_5$ is then added to the reaction mixture. The Fe(CO)$_5$ may be added while maintaining the temperature of the reaction mixture within the aforementioned levels. The Fe(CO)$_5$ may be added in multiple portions so as to avoid violent Fe(CO)$_5$ reflux. The Fe(CO)$_5$, amine, and ammonium salt ligands react thereby forming a plurality of Fe/Fe$_3$O$_4$ core/shell nanoparticles on the support. The Fe/Fe$_3$O$_4$ nanoparticles initially comprise an outer organic ligand monolayer formed from the ligands or portions thereof. These ligands can be removed prior to use of the nanocatalyst or during a first run of the nanocatalyst in a CO$_2$ hydrogenation reaction. In order to remove the ligand monolayer, the nanocatalyst is heated to a temperature above 300° C., and preferably in the presence of either H$_2$ or CO.

After the reacting step, the nanoparticles may be recovered from the reaction vessel. Typically, the nanocatalyst is permitted to cool to room temperature and then washed (such as with hexane followed by ethanol) to remove free or unattached ligands, and then dried and recovered as a fine powder. Methods of synthesizing unsupported Fe/Fe$_3$O$_4$ nanoparticles are very similar to that described above, except that the support material is not introduced into the initial reaction mixture.

In use, the nanocatalyst is contacted with a gas feedstock to produce a mixture of hydrocarbons wherein the majority (≥51% by weight) of the reaction product mixture is aromatic hydrocarbons, preferably C6-C9 aromatic hydrocarbon compounds such as mesitylene, xylenes, toluene, benzene, and mixtures thereof. Preferably, greater than about 75% by weight of the reaction product comprises aromatic hydrocarbons, and more preferably greater than about 85% by weight of the reaction product comprises aromatic hydrocarbons, and even more preferably greater than about 90% by weight of the reaction product comprises aromatic hydrocarbons. The reaction product preferably comprises less than about 30% by weight waxy solids or semisolids (e.g., paraffins), more preferably less than about 20% by weight, and even more preferably less than about 10% by weight waxy solids or semisolids. In addition to providing a high concentration of aromatic hydrocarbon compound reaction products, in certain embodiments of the present invention the distribution of reaction products comprising greater than 1% by weight of the overall reaction product composition is limited to fewer than 15 hydrocarbon compounds, fewer than 12 hydrocarbon compounds, fewer than 10 hydrocarbon compounds or fewer than 8 hydrocarbon compounds. In other embodiments, the aromatic hydrocarbon compound distribution is even narrower with mesitylene, o-xylene, p-xylene, m-xylene, toluene and benzene comprising the majority of aromatic hydrocarbon compounds produced. Various aliphatic hydrocarbon compounds such as propane and butane may also be produced, but each generally in amounts of less than 10%, less than 7.5%, less than 5%, or less than 3% by weight.

More specifically, a reaction vessel or reactor is provided, which contains the nanocatalyst. The nanocatalyst can be on a non-reactive support substrate, as described above, in the reaction vessel, or the nanocatalyst can be suspended in a magnetic field in the reaction vessel. A gas feedstock is introduced into the reaction vessel. The feed stream will comprise a source of carbon atoms and a source of hydrogen atoms. In certain embodiments, the feed stream may comprise CO$_2$, H$_2$, CO, and/or H$_2$O, sources of CO$_2$, H$_2$, CO (e.g., C1-C5 aliphatic hydrocarbon compounds), and/or H$_2$O, and/or mixtures thereof. In some embodiments a system using separate feed streams to deliver the feedstock to the reaction vessel for some or all of the feedstock gasses (or water) can be used. Advantageously, the catalyst is not dependent on the exact ratio of CO$_2$ and H$_2$ (9/24 in the reaction above) in the feedstock and is able to produce principally the same (aromatic) products even when the input concentrations of CO$_2$ and H$_2$ vary, oscillate, etc. However, in certain embodiments the molar ratio of H$_2$ to CO$_2$ is from about 1:5 to about 5:1, from about 1:1 to about 4:1, or from about 1.5:1 to about 3:1. This makes this catalyst ideal for the production of fuel from syngas. If H$_2$ is not available, the catalyst can convert CO and H$_2$O to CO$_2$ and H$_2$ via the following reaction scheme:

$$CO+H_2O \rightarrow H_2+CO_2$$

$$9CO_2+24H_2 \rightarrow C_9H_{12}+18H_2O$$

CO is available as a refinery by-product, or from pyrolytic reactions. This process can be used to enhance the efficiency of traditional refining by using CO by-product to form aromatic hydrocarbons.

Hydrogen can be generated by partial oxidation of methane (e.g., from shale gas, a source of H$_2$):

$$CH_4+H_2O \rightarrow 3H_2+CO$$

$$CH_4+0.5O_2 \rightarrow 2H_2+CO$$

Hydrogen can be also generated by thermolysis of biomass or municipal waste creating "syngas" (CO and H$_2$). The synthesis of aromatic hydrocarbons permits more consumption of CO$_2$ than is necessary for the hydrogen production (when using biomass or natural gas).

It will be appreciated that the feedstock can be delivered using any suitable system, including storage systems such as a gas cylinder or other container, as well as the direct or indirect product from another process. The gas feedstock will be reacted with the nanocatalyst in the reaction vessel. The reaction temperature will range from about 300° C. to about 560° C., about 380° C. to about 500° C., or from about 400° C. to 450° C. In certain embodiments, elevated pressures are not required for the reaction, which can typically be carried out at 1 to 10 atm, more preferably at 1 to 1.1 atm. However, elevated pressures from 1.1-100 atm may be used if desired. The reaction yields a product stream that can be collected from the reaction vessel. The reaction can be carried out for a time period of from about 20 to about 120 minutes, and preferably from about 30 to about 60 minutes before collecting the product stream from the reaction vessel. A continuous reaction process could also be used. Advantageously, the nanocatalyst can be used for multiple passes or runs (i.e., reactions) without losing its efficiency or needing to be regenerated. In some embodiments, the nanocatalyst can be used for at least about 10 reactions ("catalytic cycles") before being regenerated, and more preferably at least about 15 reactions before being regenerated. It is estimated that one mol of catalyst is able to convert 10,000-50,000 moles of CO$_2$ before the catalyst needs to regenerated.

The process is advantageous for carrying out the direct formation of aromatic hydrocarbons in a single reaction vessel via a single reaction process, without the need to further refine the reaction product to yield aromatic hydrocarbons. As disclosed herein, the reaction temperature can be adjusted to control the reaction products and target the formation of specific aromatic compounds. The aromatic hydrocarbons can be used directly as fuels or additives without the need for further refining.

Reaction Mechanism

It is well accepted that the formation of aliphatic hydrocarbons from iron catalyzed CO$_2$ hydrogenation reactions proceeds through a 2-step reaction process: first, conversion of CO$_2$ to CO via the reverse water gas shift reaction (RWGS); and second, building up hydrocarbon chains by Fischer-Tropsch reaction (FT). See, Scheme 1.

Scheme 1: Commonly accepted mechanisms of iron catalyzed $CO_2$ hydrogenation reactions $$CO_2 + H_2 \leftrightarrows CO + H_2O \quad (1)$$

$$CO + 2H_2 \rightarrow CH_2\!-\!+H_2O \quad (2)$$

$$2CO \rightarrow CO_2 + C \quad (3)$$

$$C + 2CO \rightarrow C_3O_2 \quad (4)$$

The following mechanism has been proposed for the selective formation of aromatic hydrocarbons in the $Fe/Fe_3O_4$ nanoparticle catalyzed $CO_2$ hydrogenation reaction according to certain embodiments of the present invention. In the first step, an iron nanoparticle catalyzed reverse water gas shift (RWGS) reaction produces CO from $CO_2$. This reaction permits that either $H_2$ or CO can be used as starting materials for the synthesis of fuels. The versatility of the catalyst is established by the fact that CO can be synthesized by incomplete combustion of basically all organic materials (including biomass and waste).

$$CO_2 + H_2 \leftrightarrows CO + H_2$$

In the second step, CO reacts with CO under deposition of carbon on the nanocatalyst's surface for the formation of $CO_2$. Two molecules of carbon monoxide react with each other at the surface of Fe or $Fe_3O_4$ to form one carbon atom and one molecule of carbon dioxide. This reaction leads to the deposition of carbon onto the catalyst. However, graphite has a tendency to form planar layers, where $Fe/Fe_3O_4$ nanoparticles feature an extreme curvature that prevents the formation of carbon layers and thus the deactivation of the catalyst. It is believed that nanocatalysts possessing a diameter, which is smaller than 20 nm are protected from carbon layer formation by their size. Carbon is stored as $Fe_3C$.

$$2CO \rightarrow C + CO_2$$

In the third step CO reacts with the freshly deposited carbon on the catalyst to yield carbon suboxide ($C_3O_2$). One carbon atom and two molecules of carbon monoxide form one molecule of carbon suboxide ($C_3O_2$). This molecule is the main product that is found at lower temperatures (300 to 400° C.) in the GC/MS product analysis.

$$C + 2CO \rightarrow O\!=\!C\!=\!C\!=\!C\!=\!O$$

Figure 2:
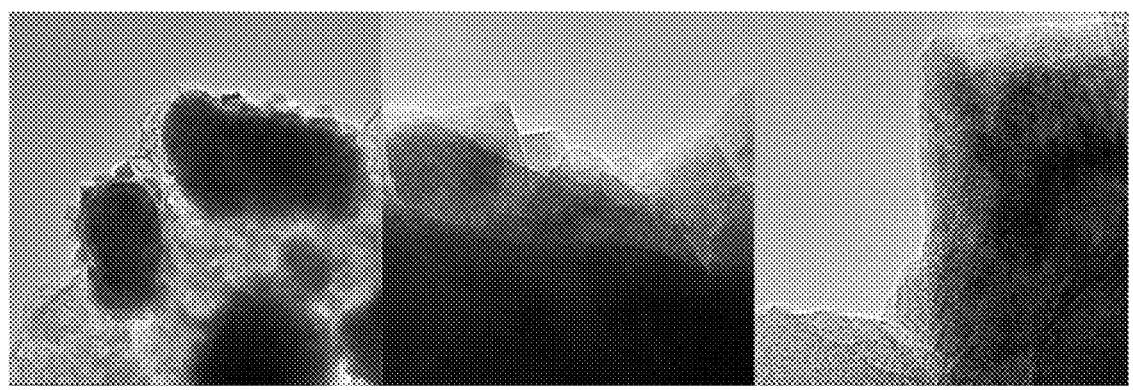
FIG. 2 is a TEM and HRTEM of Fe/Fe$_3$O$_4$ nanoparticles prepared by thermal decomposition of Fe(CO)$_5$ in the presence of oleylamine and HADxHCl after performing 10 catalytic cycles.

As illustrated by Scheme 2, below, $C_3O_2$ then undergoes trimerization to form a precursor of trimethyl benzene. This step is supported by the lattice of the new iron-containing material, which is depicted in FIG. 2. This precursor is then stepwise reduced by $H_2$ to mesitylene, the symmetrical trimethyl-benzene ($C_9H_{12}$), which is the primary initial reaction product.

Scheme 2: Proposed mechanism of the trimerization and subsequent hydrogenation of carbon suboxide ($C_3O_2$).

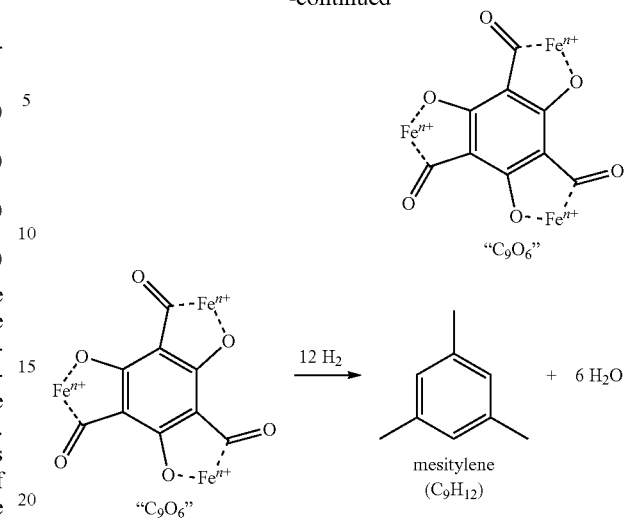

As illustrated by Scheme 3, below, at high temperature and in the presence of the iron nanocatalyst, mesitylene then undergoes stepwise de-methylation to form xylenes, toluene, and finally, benzene. Temperature can be used to control the liquid hydrocarbons formed. The byproduct of this reaction comprises, consists of, or consists essentially of propane ($C_3H_8$). However, the reduction of $C_3O_2$ by $6H_2$ is also able to form propane.

Scheme 3: Stepwise demethylation and isomerization of mesitylene at the surface of the Fe-containing nanocatalyst.

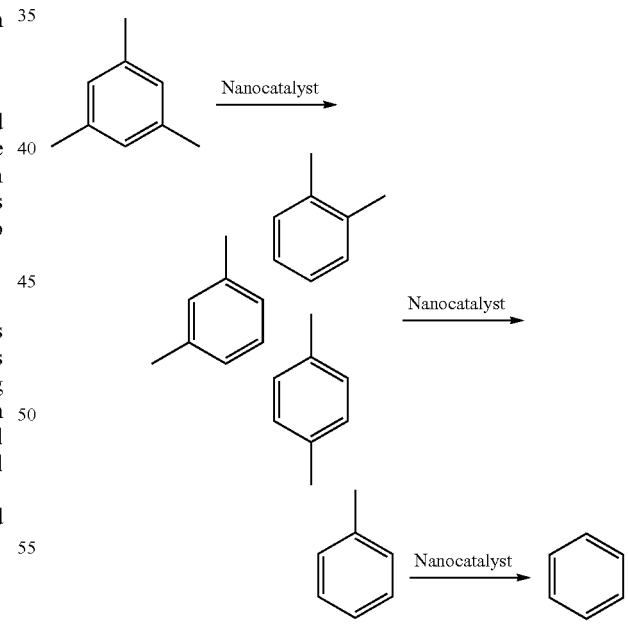

As shown in the Example 4, below, selection of the non-reactive support material has been demonstrated to affect reaction product composition, namely product distribution. While not wishing to be bound by any theory, it is believed that the support material does not catalyze the aromatic hydrocarbon-synthesizing reactions, as in certain embodiments a relatively narrow distribution of reaction products is achieved and such would not be the case if, for example, a zeolite catalyst was employed. The hydrocarbon product mixture can be readily separated from $H_2$ and $CO_2$ by condensation, and various individual aromatic hydrocarbon compounds by distillation.

Lignin Decomposition by the $Fe/Fe_3O_4$ Nanocatalyst

The nanocatalysts are also able to depolymerize lignin. Approximately 30 percent of all plant-based biomass comprises lignin, which is a crosslinked racemic macromolecule ($M_m$>10,000, poly-dispersity >1.5) composed via radical-radical coupling of p-coumaryl alcohol, coniferyl alcohol, sinapyl alcohol and other low molecular weight components. Lignin is a low cost abundant by-product of cellulosic biofuel production and or the paper industry. However, lignin cannot be used for anything except heating purposes, because it is chemically very stable. Example 2 below describes an experiment in which lignin is reacted with hydrogen gas in the presence of a $Fe/Fe_3O_4$ nanocatalyst in accordance with the present invention resulting in the formation of aromatic and aliphatic hydrocarbon compounds.

EXAMPLES

The following examples set forth materials and methods in accordance with embodiments of the present invention. It is to be understood, however, that these examples are provided by way of illustration and nothing therein should be taken as a limitation upon the overall scope of the invention.

Example 1

In this example, the selective formation of aromatic hydrocarbons from $CO_2$ hydrogenation reactions catalyzed by a $Fe/Fe_3O_4$ nanocatalyst are discussed.

Synthesis of $Fe/Fe_3O_4$ Nanoparticles

Recently, a facile method to synthesize highly crystalline $Fe/Fe_3O_4$ nanoparticles was reported by Lacroix et al., Nano Lett 2011, 11, 1641. These nanoparticles were found to be robust against deep oxidation because of the formation of protective crystalline $Fe_3O_4$ shell upon the direct oxidation of the bcc-Fe core. The highly crystalline $Fe/Fe_3O_4$ nanoparticles were chosen as the catalyst for the $CO_2$ hydrogenation reaction, as it was proposed that the unique "hardness" of this nano-structure would prevent the deactivation of the nanocatalyst by sintering at elevated reaction temperature. The $Fe/Fe_3O_4$ nanoparticles were synthesized according to the published procedure with some modifications. The reaction was also scaled up by a factor of three.

A 250 mL, three-necked, round-bottom flask equipped with a magnetic stir bar, one cold water cooled jacket condenser on the middle neck, one septum and one temperature probe on each of the outer necked was charged with 60 mL 1-octadecene (ODE), 0.9 mL oleylamine and 0.831 g hexadecylammonium chloride (HAD HCl). The reaction system was connected to a Schlenk line through the top of the jacket condenser. The reaction mixture was degassed at 120° C. for 30 min with vigorous stirring. After refilling with argon, the reaction mixture was heated to 180° C. To avoid violent $Fe(CO)_5$ reflux, three portions of 0.70 mL $Fe(CO)_5$ were added to the ligands (oleylamine and HAD HCl) and solvent (ODE) mixture via syringe every 20 min at 180° C. instead of adding the iron precursor all at one time. After the third addition, the reaction mixture was kept for 40 min at 180° C. to permit controlled nanoparticle growth, and then allowed to cool down to RT. After decanting of the supernatant, the nanoparticles that were accumulated on the magnetic stirring bar were thoroughly washed with hexane and then ethanol (sonication) to remove the free ligands. The NPs were dried in high vacuum, and the yield based on iron was found to be 95%. After synthesis, the $Fe/Fe_3O_4$ particles were found to have diameters between 10 nm and 20 nm. They also feature an organic ligand sphere. This ligand sphere is removed at temperatures above 300° C. in the presence of either hydrogen or carbon monoxide.

Characterization of the Catalysts

As shown in FIG. 1, the TEM image reveals that the newly synthesized $Fe/Fe_3O_4$ nanoparticles are roughly spherical with a core/shell structure. The mean core diameter is 12 nm, and the shell thickness is 2 nm. HRTEM indicate that each $Fe/Fe_3O_4$ nanoparticle assumes polycrystalline structure with rigid edges.

The XRD characterization confirmed the crystalline structure of the $Fe/Fe_3O_4$ nanoparticles. The (110) and (200) peaks corresponded to bcc-Fe. XRD characterization was repeated after exposing the nanoparticles to air at room temperature for 2 months, and no noticeable change could be discerned from the XRD patterns as compared to these of the freshly-made sample.

Whereas the nanocatalyst are comprised mainly of Fe(0) and amorphous material before reaction, as XRD indicates, Fe(0), $Fe_3O_4$, FeO and iron-oxide bound water are discernible after 10 catalytic cycles.

$CO_2$ Hydrogenation Reaction

The $Fe/Fe_3O_4$ nanoparticle-catalyzed $CO_2$ hydrogenation reaction was performed in a home-built reactor. 50 mg of $Fe/Fe_3O_4$ nanoparticles were subjected to a continuous supply of (1:1 mol/mol) $CO_2/H_2$ atmosphere at 1-1.1 atm pressure. Gas samples were withdrawn from the reactor and analyzed by GC-MS during the reaction. Upon heating from room temperature (RT) to 400° C., traces of butane (2.881 min), benzene (4.135 min) and toluene (5.819 min) were observed, together with a major peak (2.989 min) and minor peak (5.765 min) in the GC profile corresponding to 68 and 71 mass units. These two species were assigned to carbon suboxide ($C_3O_2$) and its partially reduced form ($C_3O_2H_3$). Upon raising the temperature to 440° C., three new peaks at (7.915 min, 8.100 min, 8.688 min), all corresponding to 106 mass units, appeared. By comparing with commercially available standard samples, these three peaks were identified as m-xylene, p-xylene and o-xylene, respectively. The reaction temperature was raised with a rate of 1° C./min afterwards, and gas samples were subjected to GC-MS analysis every 20 mins. It was found that with the increase of reaction temperature, the intensity of the peak at 2.989 min ($C_3O_2$) decreased gradually. At the same time, the intensity of the benzene peak (4.135 min) and toluene peak (5.819 min) increased. At 480° C., the peaks at 2.989 min (C302) disappeared completely, while the peak at 5.765 min ($C_3O_2H_3$) still persisted until the temperature reached 500° C. Further increasing temperature to 520° C. led to the decrease of the xylenes' peaks. The decrease of the toluene peak and the increase of the benzene peak were observed while keeping the reaction at 520° C. for 40 min.

Heating of $CO_2/H_2$ in the absence of nanocatalyst and heating of the catalyst under nitrogen did not result in the formation of detectable traces of aromatic compounds. Furthermore, aromatic hydrocarbons have been formed at a $CO_2$ to $H_2$ ratio of 1:1 and 2:1 mol/mol) indicating that the chemical nature of the formed reduction products of carbon dioxide is not strongly dependent on the chemical composition of the $CO_2/H_2$ mixture.

Alternative Nanoparticle Synthesis Method Using Tetraethylammonium Chloride as Additive A 100 mL, three-necked, round-bottom flask equipped with a magnetic stir bar, one cold water cooled jacket condenser on the middle neck, one septum and one temperature probe on each of the outer necks was charged with 40 mL 1-octadecene (ODE), 0.6 mL oleylamine and 0.33 g tetraethylammonium chloride. The reaction system was connected to a Schlenk line through the top of the jacket condenser. The reaction mixture was degassed at 120° C. for 30 min with vigorous stirring. After refilled with argon, the reaction mixture was heated to 180° C. Next, 1.4 mL $Fe(CO)_5$ was injected into the reaction mixture via a syringe. The reaction mixture was kept at 180° C. for 40 min, and cooled to room temperature naturally. The supernatant was decanted, and the iron nanoparticles accumulated on the magnetic stir bar were washed with hexane and ethanol. The product was dried in vacuum and stored at room temperature for further use. Based on iron, the yield of the reaction was 90%.

Tests of the Mechanistic Paradigm

As noted above, it has been proposed that mesitylene undergoes stepwise de-methylation to form xylenes, toluene, and finally, benzene. To verify the formation of mesitylene, the $CO_2$ hydrogenation reaction was directly subjected to 520° C. using exactly the same conditions as described. A peak at 10.417 min, corresponding to mass unit 120 was observed in the GC-MS. This compound was identified as mesitylene by comparing with standard sample. This proved unambiguously that mesitylene is formed from $CO_2$ and $H_2$ at the surface of $Fe/Fe_3O_4$ nanocatalysts Reuse of Catalyst Catalyst was reused up to 18 times, with no degradation of the catalytic activity observed. This observation is based on the consumption efficiency of $CO_2$ from the gas phase and product analysis by GC-MS. Evidence from XPS studies showed that the nanocatalysts consist of crystalline alpha-Fe before the beginning of the catalytic activity. After 18 catalytic cycles, Fe(0) disappeared and $Fe_3O_4$ is the catalytic phase. Carbon is stored as $Fe_3C$. Its volume fraction increased from run 1 to run 18.

Z-Potential of the $Fe/Fe_3O_4$ Catalyst

The Zeta-potential of the $Fe/Fe_3O_4$ catalyst was measured in ethanol solution. The value was +27 mV. A range from +10 mV to +50 mV can be expected.

BET Surface of the $Fe/Fe_3O_4$ Catalyst

The BET surfaces for both preparations of $Fe/Fe_3O_4$ catalyst ranged from 20-25 and preferably 23-24 $m^2/g$, for fresh catalyst, and from 50-60 $m^2/g$, and preferably 56-57 $m^2/g$ after 10 runs (reactions). However, as noted above, despite some build up of carbon at the surface, the efficiency of the catalysts remains relatively stable even after repeated passes.

Example 2

In this example, lignin is reacted with Hz in the presence of a $Fe/Fe_3O_4$ catalyst prepared as described above to produce various aromatic hydrocarbon compounds. 150 mg of lignin and 20 mg $Fe/Fe_3O_4$ MNPs were mixed by grinding. The solid mixture was charged to a ceramic boat and slid into the reactor. After pulling a vacuum for 3 hours, the reactor was refilled with Hz, and then the temperature was increased to 460° C. GC-MS performed on the reaction product after 20 minutes of reaction time shows the formation of xylenes, toluene, benzene, propane, butane and other cyclic hydrocarbons.

Example 3

In this example, the preparation of an α-alumina supported $Fe/Fe_3O_4$ nanocatalyst and a zeolite supported $Fe/Fe_3O_4$ nanocatalyst and selective formation of aromatic hydrocarbons from $CO_2$ hydrogenation reactions catalyzed by the nanocatalysts are discussed.

Preparation of α-Alumina Supported $Fe/Fe_3O_4$

A 250 mL, three-necked, round-bottom flask equipped with one mechanical stirrer, one cold water cooled jacket condenser, one temperature probe on each of the outer necks was charged with 120 mL 1-octadecene (ODE), 1.80 mL oleylamine, 1.75 g hexadecylammonium chloride (HAD HCl) and 10 g pre-dried α-alumina. The reaction system was connected to a Schlenk line through the top of the jacket condenser. The reaction mixture was degassed at 120° C. for 30 min with vigorous stirring. After being refilled with argon, the reaction mixture was heated to 180° C., and then 5 mL $Fe(CO)_5$ was injected into the reaction mixture via a syringe. The reaction mixture was kept at 180° C. for 30 min, and cooled to room temperature naturally. After shortly applying a magnet underneath the flask, the supernatant was decanted to three 50 mL centrifuge tubes evenly. The α-alumina supported $Fe/Fe_3O_4$ particles were collected by centrifugation at 4000 RPM and washed with hexane and ethanol sequentially. After being dried under vacuum, 9.6 g of black powder was obtained.

Preparation of Zeolite Y Supported $Fe/Fe_3O_4$

A 250 mL, three-necked, round-bottom flask equipped with one mechanical stirrer, one cold water cooled jacket condenser, one temperature probe on each of the outer necks was charged with 120 mL 1-octadecene (ODE), 1.80 mL oleylamine, 1.75 g hexadecylammonium chloride (HAD HCl) and 4.3 g pre-dried zeolite Y. The reaction system was connected to a Schlenk line through the top of the jacket condenser. The reaction mixture was degassed at 120° C. for 30 min with vigorous stirring. After being refilled with argon, the reaction mixture was heated to 200° C., and then 3 mL $Fe(CO)_5$ was injected into the reaction mixture via a syringe. The reaction mixture was kept at 180° C. for 30 min, and cooled to room temperature naturally. After shortly applying a magnet underneath the flask, the supernatant was decanted to three 50 mL centrifuge tubes evenly. The zeolite Y supported $Fe/Fe_3O_4$ particles were collected by centrifugation at 4000 RPM and washed with hexane and ethanol sequentially. After being dried under vacuum, 4.0 g of a black powder was obtained.

Characterization of Solid Supported $Fe/Fe_3O_4$ Catalysts

Figure 3:
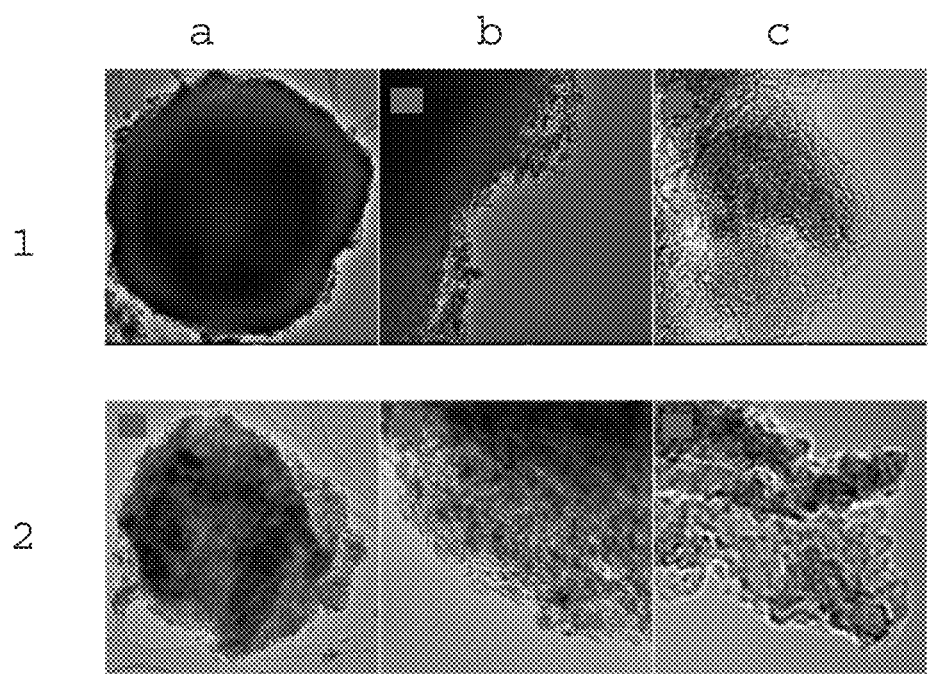
FIG. 3 is a TEM of α-Al$_2$O$_3$ supported Fe/Fe$_3$O$_4$ made in accordance with an embodiment of the present invention.

FIG. 3 shows representative TEM micrographs of the α-$Al_2O_3$ supported $Fe/Fe_3O_4$ both for fresh catalyst (1a, 1b, 1c) and catalyst recycled after 5 runs (2a, 2b, 2c). Homogeneous distribution of iron nanoparticles on the surface of α-$Al_2O_3$ is illustrated. The $Fe/Fe_3O_4$ particle assume rod-like shape on this support. Both the morphology and size of the supported particles did not change over 5 runs of catalytic cycles.

Figure 4:
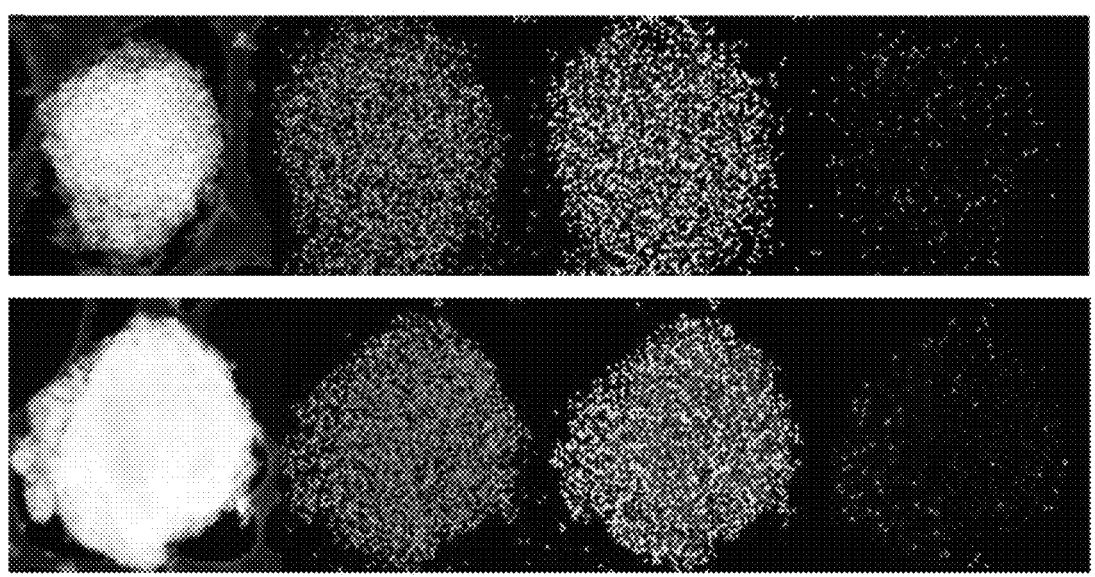
FIG. 4 is an STEM showing elemental mapping for the fresh α-Al$_2$O$_3$ supported Fe/Fe$_3$O$_4$ catalyst (top row) and the catalyst after 5 runs (bottom row)

EDX characterization revealed that, for the fresh catalyst, 9.49% iron (by weight) was loaded on the α-$Al_2O_3$ support. After 5 runs of catalytic cycles, iron content dropped to 7.50%. The change of iron content may be due to the oxidation of the Fe(0) core over the catalytic reaction. Scanning transmission electron microscope (STEM) of the catalyst further confirmed the homogeneous distribution of iron particles on the solid support. The STEM is shown in FIG. 4 with the top row showing elemental mapping for the fresh catalyst, and the bottom row showing elemental mapping for the catalyst after 5 runs.

Figure 5:
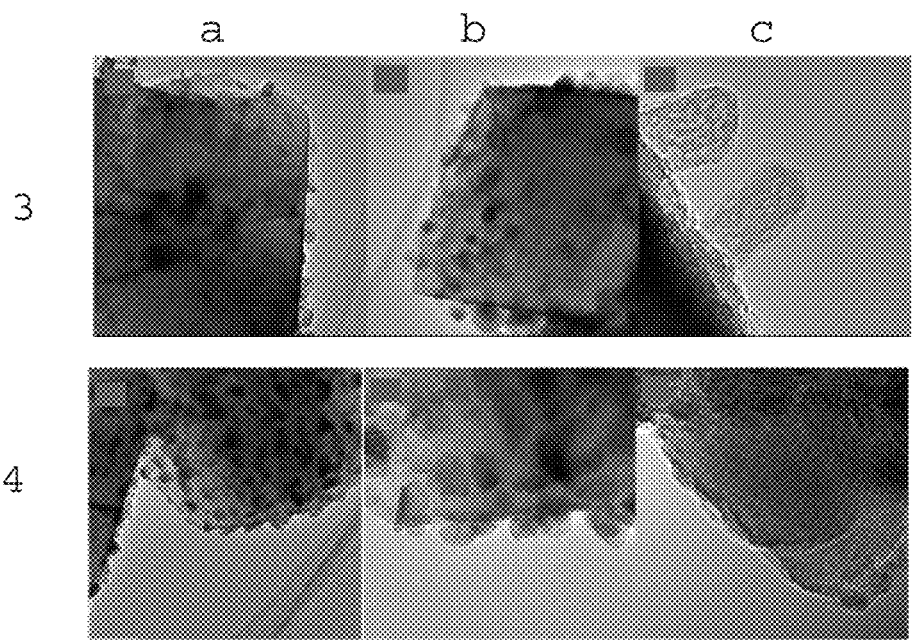
FIG. 5 is a TEM of zeolite Y supported Fe/Fe$_3$O$_4$ catalyst made in accordance with an embodiment of the present invention.

FIG. 5 shows representative TEM micrographs of the zeolite Y supported $Fe/Fe_3O_4$ both for before catalysis (3a, 3b, 3c) and after 5 runs (4a, 4b, 4c). Due to the porous nature of zeolite Y, $Fe/Fe_3O_4$ nanoparticles were deposited both on the surface and inside the pores of the solid support. The deposited $Fe/Fe_3O_4$ particle assumed irregular shapes on this support. Both the morphology and size of the supported particles did not change over 5 runs of catalytic cycles.

Figure 6:
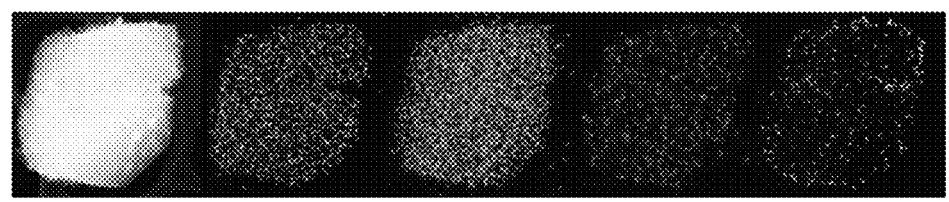
FIG. 6 is an STEM showing elemental mapping for the fresh zeolite Y supported Fe/Fe$_3$O$_4$ catalyst (top row) and the catalyst after 5 runs (bottom row).
Figure 6:
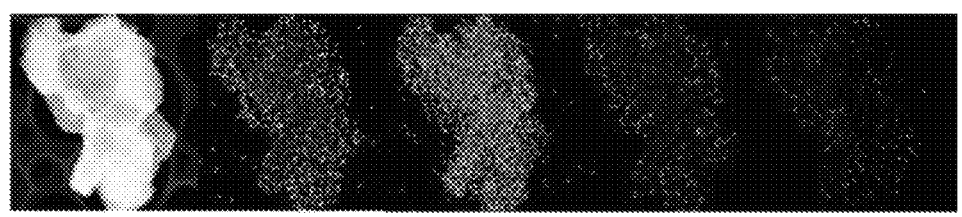

EDX characterization revealed that, for the fresh catalyst, 10.64% iron (by weight) was loaded on the zeolite Y support. After 5 runs of catalytic cycles, iron content increased to 11.70%. Scanning transmission electron microscope (STEM) demonstrated that $Fe/Fe_3O_4$ distributed on zeolite Y supported homogeneously, and the iron distribution didn't change over catalytic cycles. The STEM is shown in FIG. 6 with the top row showing elemental mapping for the fresh catalyst, and the bottom row showing elemental mapping for the catalyst after 5 runs.

$CO_2$ Hydrogenation Catalyzed by Solid Supported $Fe/Fe_3O_4$

In each trial, 150 mg solid supported $Fe/Fe_3O_4$ catalyst in a ceramic boat was inserted into the reactor. The catalyst was heated to 350° C. under high vacuum for 2 hours to remove any absorbed organic molecules. After cooling to room temperature, the reactor was refilled with 120 mL of 1/1 $CO_2/H_2$ mixture at 1 atm pressure. The reactor was equipped with a magnetic-driven fan to enhance the gas flow over the solid catalysts. The circulating fan was regulated by an external magnetic stirrer. The reaction temperature was brought to 400° C. in 20 min. Gas samples were withdraw from the reactor and analyzed via GC-MS. 1,3,5-trimethylbenzene was found to be the major product with both solid supported catalysts. Within 1 hour, demethylation products, such as xylenes, toluene and benzene were observed. Each catalyst was reused for 5 runs, and no major loss of activity was observed.

Example 4

In this example, the effect of the support material composition on aromatic hydrocarbon product selectivity was studied. $CO_2$ hydrogenation reactions were catalyzed with α-alumina supported $Fe/Fe_3O_4$ nanocatalyst and zeolite Y supported $Fe/Fe_3O_4$ nanocatalyst prepared as described in Example 3. Each catalyst comprised approximately 10±2% $Fe/Fe_3O_4$ content (by weight). The reactor was loaded with the respective solid-supported $Fe/Fe_3O_4$ nanocatalyst and absorbed organic molecules were removed as described in Example 3. A 1/1 $CO_2/H_2$ molar ratio mixture was introduced into the catalyst-filled reactor at 1 atm pressure and 480° C. After reacting for two hours, gas samples were withdrawn and analyzed via GC-MS. The results are provided in Table 1.

TABLE 1

| Reaction Product | α-alumina supported $Fe/Fe_3O_4$ (% by weight) | zeolite Y supported $Fe/Fe_3O_4$ (% by weight) |
|---|---|---|
| Mesitylene | 40% | 13% |
| p-Xylene | 16% | 13% |
| m-Xylene | 13% | 16% |
| o-Xylene | 12% | 14% |
| Toluene | 8% | 27% |

TABLE 1-continued

| Reaction Product | α-alumina supported $Fe/Fe_3O_4$ (% by weight) | zeolite Y supported $Fe/Fe_3O_4$ (% by weight) |
|---|---|---|
| Benzene | 3% | 8% |
| Butane | 2% | 3% |
| Propane | 5% | 4% |

Based on these results, the solid α-alumina support appears to enhance the formation of mesitylene and the solid zeolite Y support appears to enhance the formation of toluene and xylenes. Accordingly, product selectivity can be controlled based upon selection of the non-reactive support material. Moreover, the results demonstrate that the reaction results in formation of a fairly narrow product distribution in that greater than 90% of the reaction products, for each catalyst, were aromatic hydrocarbon compounds, and only two non-aromatic compounds were produced in meaningful quantities.

In certain embodiments, the present invention may further include a method of synthesizing $Fe/Fe_3O_4$ core/shell nanoparticles on a non-reactive support material comprising the steps of:

providing a reaction mixture within a reaction vessel, said reaction mixture comprising a C10-C24 alkene solvent, a C10-C24 amine having at least one ethylenically unsaturated group, a C4-C24 ammonium salt, and a non-reactive support material; heating said reaction mixture to a temperature of between about 150° C. to about 210° C.;

adding to said reaction mixture a quantity of $Fe(CO)_5$;

reacting said $Fe(CO)_5$, said C10-C24 amine, and said C4-C24 ammonium salt so as to form a plurality of $Fe/Fe_3O_4$ core/shell nanoparticles on said non-reactive support, said $Fe/Fe_3O_4$ nanoparticles comprising an outer organic ligand monolayer formed from at least portions of said C10-C24 amine and/or said C4-C24 ammonium salt; and recovering said $Fe/Fe_3O_4$ nanoparticles on said non-reactive support from said reaction vessel.

In certain embodiments, the C10-C24 alkene solvent is 1-octadecene.

In certain embodiments, the C4-C24 ammonium salt is selected from the group consisting of C8-C22 primary alkyl ammonium salts, C4-C24 quaternary alkyl ammonium salts, and combinations thereof.

In certain embodiments, the C4-C24 ammonium salt is hexadecylammonium chloride and/or tetraethylammonium chloride.

In certain embodiments, the C10-C24 amine is oleylamine

In certain embodiments, the reaction mixture is heated to about 180° C. prior to addition of said $Fe(CO)_5$.

In certain embodiments, the reacting step is performed while maintaining said reaction mixture at a temperature of between about 150° C. to about 210° C.

In certain embodiments, after the reacting step, said $Fe/Fe_3O_4$ nanoparticles are cooled to room temperature, washed to remove free ligands, and dried.

In certain embodiments, following the recovering step, said $Fe/Fe_3O_4$ nanoparticles are heat treated at a temperature above 300° C. to remove at least a portion of said outer organic ligand monolayer.

In certain embodiments, the non-reactive support material is selected from the group consisting of zeolites and α-alumina.

We claim:

1. A method of synthesizing one or more aromatic hydrocarbon compounds comprising:
   providing within a reactor a quantity of a catalytic material comprising $Fe/Fe_3O_4$ core/shell nanoparticles;
   introducing into said reactor and contacting said catalytic material with a quantity of reactants comprising a source of carbon atoms and a source of hydrogen atoms;
   reacting said reactants within said reactor under conditions for forming said one or more aromatic hydrocarbon compounds; and
   recovering said one or more aromatic hydrocarbon compounds from said reactor.

2. The method according to claim 1, wherein said source of carbon atoms is selected from the group consisting of a biomass material, $CO_2$, CO, and combinations thereof.

3. The method according to claim 2, wherein said source of carbon atoms comprises $CO_2$ and/or CO.

4. The method according to claim 2, wherein said biomass material comprises lignin.

5. The method according to claim 1, wherein said source of hydrogen atoms is selected from the group consisting of $H_2$, $H_2O$, $CH_4$, and combinations thereof.

6. The method according to claim 1, wherein said reacting step within said reactor occurs at a pressure of between about 1 to about 100 atm.

7. The method according to claim 6, wherein said reacting step within said reactor occurs at a pressure of between about 1 to about 1.1 atm.

8. The method according to claim 1, wherein said reacting step within said reactor occurs at a temperature of between about 380° C. to about 560° C.

9. The method according to claim 1, wherein said reactor operates as a batch reactor, said catalyst undergoing at least 10 reaction cycles prior to being regenerated.

10. The method according to claim 1, wherein said one or more aromatic hydrocarbon compounds recovered from said reactor are selected from the group consisting of xylenes, toluene, benzene, and mixtures thereof.

11. The method according to claim 1, wherein said one or more aromatic hydrocarbon compounds recovered from said reactor are directly usable as a fuel in an internal combustion engine upon recovery from said reactor without under going further refinement.

12. The method according to claim 1, wherein said source of carbon atoms is not subjected to thermolysis prior to being introduced into said reactor.

13. The method according to claim 1, wherein said nanoparticles are supported on a non-reactive support substrate.

14. The method according to claim 13, wherein said non-reactive support substrate comprises a zeolite.

15. A method of synthesizing one or more aromatic hydrocarbon compounds comprising:
   providing within a reactor a quantity of a catalytic material comprising $Fe/Fe_3O_4$ core/shell nanoparticles;
   introducing into said reactor and contacting said catalytic material with a quantity of reactants comprising a source of carbon atoms and a source of hydrogen atoms, said source of carbon atoms being selected from the group consisting of lignin, $CO_2$, CO, and combinations thereof, said source of hydrogen atoms being selected from the group consisting of $H_2$, $H_2O$, $CH_4$, and combinations thereof;
   reacting said reactants within said reactor under conditions for forming said one or more aromatic hydrocarbon compounds, said conditions within said reactor comprise a temperature of between about 380° C. to about 560° C., and a pressure of between about 1 to about 1.1 atm; and
   recovering said one or more aromatic hydrocarbon compounds from said reactor, said one or more aromatic hydrocarbon compounds being selected from the group consisting of xylenes, toluene, benzene, and mixtures thereof, said aromatic hydrocarbon compounds comprising at least 75% by weight of the total reaction products produced by said reacting step.

16. A system for synthesizing one or more aromatic hydrocarbon compounds comprising:
   a reactor comprising a quantity of a catalytic material comprising $Fe/Fe_3O_4$ core/shell nanoparticles;
   one or more reactant feed streams coupled with said reactor and operable to deliver to said reactor a source of carbon atoms and a source of hydrogen atoms;
   said reactor operating under conditions for reacting said source of carbon atoms and said source of hydrogen atoms in the presence of said catalytic material and forming said one or more aromatic hydrocarbon compounds; and
   a reaction product discharge stream coupled with said reactor and operable to remove said one or more aromatic hydrocarbon compounds from said reactor.

17. The system according to claim 16, wherein said nanoparticles are supported on a non-reactive support substrate.

18. The system according to claim 16, wherein said reactor is a batch reactor, said catalytic material being capable of undergoing at least 10 reaction cycles prior to being replaced or regenerated.

19. The system according to claim 16, wherein said reactor is a continuous reactor, and said source of carbon atoms comprises $CO_2$, one mole of said catalytic material being capable of converting between 10,000 to 50,000 moles of $CO_2$ into said one or more hydrocarbon compounds before the catalyst needs to be regenerated.

20. The system according to claim 16, wherein said reactor operates at a temperature of between about 380° C. to about 560° C., and a pressure of between about 1 to about 1.1 atm.

21. The system according to claim 16, wherein said source of carbon atoms delivered to said reactor by said at least one reactant feed stream is selected from the group consisting of lignin, $CO_2$, CO, and combinations thereof.

22. The system according to claim 16, wherein said source of hydrogen atoms delivered to said reactor by said at least one reactant feed stream is selected from the group consisting of $H_2$, $H_2O$, $CH_4$, and combinations thereof.

23. The system according to claim 16, wherein said one or more aromatic hydrocarbon compounds removed from said reactor by said reaction product discharge stream are selected from the group consisting of xylenes, toluene, benzene, and mixtures thereof.

24. A catalytic material operable to catalyze a reaction resulting in the formation of one or more aromatic hydrocarbon compounds comprising: a plurality of iron/iron oxide core/shell nanoparticles having an average diameter of less than about 20 nm on a non-reactive support substrate, wherein said iron oxide consists of $Fe_3O_4$.

25. The catalytic material according to claim 24, wherein said non-reactive support substrate comprises a zeolite.

26. The catalytic material according to claim 24, wherein said nanoparticles comprise crystalline core and shell structures.

27. The catalytic material according to claim 24, wherein said nanoparticles comprise an organic ligand monolayer adjacent said shell.

28. The catalytic material according to claim 24, wherein said nanoparticles are free of silane coatings.

29. A catalytic material operable to catalyze a reaction resulting in the formation of one or more aromatic hydrocarbon compounds comprising: a plurality of $Fe/Fe_3O_4$ core/shell nanoparticles having an average diameter of less than about 20 nm on a non-reactive support substrate, wherein said non-reactive support substrate comprises a zeolite.

30. A catalytic material operable to catalyze a reaction resulting in the formation of one or more aromatic hydrocarbon compounds comprising: a plurality of $Fe/Fe_3O_4$ core/shell nanoparticles having an average diameter of less than about 20 nm on a non-reactive support substrate, wherein said nanoparticles comprise an organic ligand monolayer adjacent said shell.

* * * * *